United States Patent

Colin et al.

[11] Patent Number: 5,773,307
[45] Date of Patent: Jun. 30, 1998

[54] METHOD AND DEVICE FOR DETERMINING AN ANALYTE IN A SAMPLE

[75] Inventors: Bruno Colin, Tassin-la-Demi-Lune; Michel Goudard, Saint-Genis-les-Ollières; Alain Theretz, Ecully, all of France

[73] Assignee: Bio Merieux, Marcy L'Etoile, France

[21] Appl. No.: 615,204

[22] PCT Filed: Sep. 20, 1994

[86] PCT No.: PCT/FR94/01099

§ 371 Date: Mar. 11, 1996

§ 102(e) Date: Mar. 11, 1996

[87] PCT Pub. No.: WO95/08769

PCT Pub. Date: Mar. 30, 1995

[30] Foreign Application Priority Data

Sep. 20, 1993 [FR] France ................. 93 11363

[51] Int. Cl.⁶ .............. G01N 33/553; G01N 33/544; C12M 1/40; B03C 1/00
[52] U.S. Cl. ............ 436/526; 436/528; 436/534; 436/806; 435/288.3; 209/214; 209/225; 210/222
[58] Field of Search ............ 436/526, 528, 436/534, 806, 518; 435/288.3; 209/214, 225; 210/222

[56] References Cited

U.S. PATENT DOCUMENTS 4,913,883  4/1990  Imai et al. ................. 436/526
5,445,971  8/1995  Rohr ........................ 436/526

FOREIGN PATENT DOCUMENTS 0339623  11/1989  European Pat. Off. .
2074727  11/1981  United Kingdom .

OTHER PUBLICATIONS

Database WPI, Week 8519, Derwent Publications Ltd., London, GB; AN 85–113585.

*Primary Examiner*—Ponnathapura Achutamurthy
*Assistant Examiner*—Padmashri Ponnaluri
*Attorney, Agent, or Firm*—Oliff & Berridge, PLC

[57] ABSTRACT

A method for determining an analyte in a sample which includes: providing the sample in liquid phase, the analyte of which has a ligand having at least one anti-ligand specific recognition site; providing at least one reagent containing metal particles, in suspension in liquid phase and non-separable from the liquid phase by a magnetic or electromagnetic force, each particle containing a metal core to which at least one anti-ligand is fixed directly or indirectly; contacting the sample and the at least one reagent in order to obtain metal clusters; placing the metal clusters in a magnetic field generated by a magnetic or magnetic field generating sensor in order to assemble the metal clusters; and detecting the assembled metal clusters to obtain a signal representative of the mass of metal in the clusters, which is correlated with the quantity of analyte present in the sample initially. A device for determining an analyte in a sample by the above process is also included.

17 Claims, 4 Drawing Sheets

METHOD AND DEVICE FOR DETERMINING AN ANALYTE IN A SAMPLE

The subject of the present invention is a method for determining an analyte which may be present in a sample.

BACKGROUND OF THE INVENTION

According to the invention, determining an analyte is understood to mean the detection and/or the assay of any substance, especially chemical, biochemical or biological.

The analyte to be determined may be, without any limitation, an antigen, a hapten, an antibody, a peptide, a nucleic acid fragment (DNA or RNA), an enzyme, a substrate, provided that the analyte comprises a ligand having at least one recognition site capable of binding specifically to a determined anti-ligand. Description of the prior art According to Patent Application EP-0,339,623, a method is described for determining an analyte in a sample which comprises:

i) providing said sample in liquid phase, the analyte of which comprises a ligand having at least one anti-ligand specific recognition site;

ii) providing at least one reagent containing metal particles a few nanometers in size, in suspension in liquid phase and non-separable from said liquid phase by magnetic or electromagnetic means, each particle containing a metal core to which at least one anti-ligand is fixed directly or indirectly;

iii) contacting, especially by incubation, the sample and the reagent, optionally with another reagent, in order to obtain metal clusters;

iv) placing the metal clusters in a magnetic field, in order to assemble the metal clusters;

v) detecting, by light diffraction, the assembled metal clusters to obtain a signal representative of the mass of metal in said clusters, correlated with the quantity of analyte present in the sample initially.

The method in accordance with document EP-A-0,339,623 has the disadvantage of resorting to a means for detecting the assembled metal clusters by magnetic field, which is particularly complex, since in practice it requires a coherent monochromatic light source (laser), a diffracted light detector and processing of the light signal thus collected.

SUMMARY OF THE INVENTION

The subject of the present invention is a method which uses a much simpler detection device, and which makes it possible to correlate precisely the metal mass of the assembled metal clusters with the quantity of analyte present in the sample.

Indeed, according to the invention, the metal mass of the said clusters is detected using a magnetic or magnetizable sensor generating the field which served to assemble the metal clusters, the said sensor being placed close to the sample and moved or subjected to a force caused by the assembled metal clusters, giving a movement or force signal representative of the metal mass of the clusters.

Of course, magnetic sensor is understood to mean any electromagnetic sensor and the like.

The terms ligand and anti-ligand as used in the present invention refer to any biological molecules capable of forming a ligand/anti-ligand complex such as the complexes antigen/antibody, antibody/hapten, hormone/receptor, protein/antibody, biotin/streptavidin, lectin/sugar, chelator/chelated molecule, oligonucleotide/oligonucleotide hybrid, oligonucleotide/nucleic acid hybrid, enzyme/substrate; it being understood that when the ligand is a nucleic acid fragment, it can react with either an RNA fragment or a DNA.

Antibody according to the invention is understood to mean monoclonal antibodies, polyclonal antibodies, antibody fragments and antibodies obtained by genetic recombination.

Particles non-separable in liquid phase by magnetic or electromagnetic means is understood to mean particles which, in the absence of a magnetic or electro-magnetic field, are not capable of sedimenting, and which, not being sedimented, in the presence of a magnetic or electromagnetic field, are chosen based on the criterion of size, so as not to be attracted by this field.

The measurement of the metal mass of the metal clusters can be performed during or after the contacting of the sample and the reagent.

According to the invention, the magnetic sensor may be for example a magnet, integrally attached to the tray of a balance, and the metal mass of the metal clusters is measured by negative weighing, that is to say by measuring the lightening of the tray.

According to the method of the invention, there is provided:

a primary reagent comprising metal particles in suspension in liquid phase, non-separable from said liquid phase by magnetic means, each particle containing a metal core to which is fixed directly or indirectly at least one anti-ligand capable of reacting with a recognition site of the analyte ligand a secondary reagent comprising metal particles in suspension in liquid phase and non-separable from said liquid phase by magnetic means, each particle containing a metal core to which is fixed directly or indirectly at least one other anti-ligand capable of reacting with another recognition site of the analyte ligand.

In one embodiment of the method of the invention, the analyte ligand comprises at least two recognition sites, which are identical or different, of the reagent anti-ligand, sufficiently far apart from each other to allow the same ligand to be combined with two anti-ligands.

In another embodiment, the reagent anti-ligand comprises two receptor sites of the analyte ligand which are sufficiently far apart from each other to allow the same anti-ligand to be combined with two ligands.

According to another embodiment of the method, the reagent anti-ligand comprises at least two receptor sites, and the analyte ligand comprises at least two recognition sites which are specific for the two receptor sites of the reagent respectively.

According to a specific embodiment, the primary reagent and secondary reagent are identical and the analyte ligand comprises at least two identical recognition sites.

When the primary and secondary reagents are identical, the primary reagent may comprise a second anti-ligand different from the first and capable of binding to a recognition site of the analyte ligand which is different from the site recognized by the first anti-ligand.

For a determination of the analyte by competition, another so-called competition reagent is provided comprising particles in suspension in liquid phase and non-separable from said liquid phase by magnetic means, each particle containing a metal core to which is fixed directly or indirectly another ligand specifically recognized by the reagent anti-ligand.

Another subject of the invention is a device for determining an analyte in a sample, comprising:

i) a container for receiving a sample to be determined in liquid phase, the analyte of which comprises a ligand having at least one anti-ligand specific recognition site ii) with at least one reagent comprising metal particles in suspension in liquid phase and non-separable from said liquid phase by magnetic means, each particle containing a metal core to which is fixed directly or indirectly at least one anti-ligand, having at least one receptor site of a ligand iii) the sample, said reagent and optionally another reagent being contacted in said container, especially by incubation, in order to obtain metal clusters iv) a magnetic means delivering a magnetic field, in which the metal clusters are placed in order to assemble them v) a means for detecting the assembled metal clusters, in order to obtain a signal representative of the mass of metal in the clusters, correlated with the quantity of analyte present in the sample initially, said means for detecting the metal mass comprising a magnetic or magnetizable sensor, which comprises the magnetic means according to iv), is placed close to the sample, and is moved or subjected to a force caused by the assembled metal clusters, giving a movement or force signal representative of the metal mass of the clusters.

In a specific embodiment, the sensor is integrally attached to a tray of a balance which delivers a negative weighing signal corresponding to the lightening of said tray, and representative of the metal mass of the clusters.

By way of example, the metal core of the particles of the reagent is chosen from materials which are intrinsically magnetic or magnetizable, such as complex salts and the oxides, borides, sulfides of iron, cobalt, nickel and the rare-earth elements, having a high magnetic susceptibility such as hematite and ferrites. The magnetic core of the particles comprises pure metals or alloys comprising one or more of these elements. The metal core is preferably chosen so that it is free of residual magnetism, and its mean size is between 5 and 30 nm, in particular 10 and 20 nm. The metal core may represent from 5 to 100% by weight, in particular from 25 to 65% by weight, of the insoluble particle.

The particles may comprise an envelope in addition to the metal core. The composition of the envelope is not critical, since it allows the attachment of ligands and of anti-ligands, and since it is capable of interacting with the metal core. By way of example, the envelope may be a natural polymer, chemically modified or otherwise, for example a polysaccharide such as agarose, dextran, cellulose derivates such as carboxymethylcellulose; a protein such as gelatin and a polymer of albumin; a synthetic polymer, chemically modified or otherwise, such as acrylic or methacrylic acids.

The mean size of the reagent particle is between 20 and 100 nm, in particular between 50 and 70 nm.

The reagent(s) are mixed with a liquid sample which is supposed to contain the analyte and therefore the ligand, and subjected for example to an incubation. The contacting of the sample and the reagent is performed at a determined pH which depends on the nature of the ligand to be detected. Although the contacting can be carried out in a very wide temperature range, from 2 to 95° C., the temperature advantageously chosen is room temperature or a temperature of between 37° C. and 40° C. The contacting time is determined as a function of the type of assay according to conventional operating conditions which are known per se.

Usually, a buffer is used to maintain the desired pH. The buffer solution which can be used may be chosen from a phosphoric acid buffer or a Tris buffer and the like. In some cases, salts, proteins or detergents are added to the mixture in order to avoid nonspecific reactions.

The present invention is now illustrated by the diagram in the annex and the following examples.

BRIEF DESCRIPTION OF THE DRAWINGS

The diagram comprises FIGS. 1 to 4 according to which.

Figure 1:
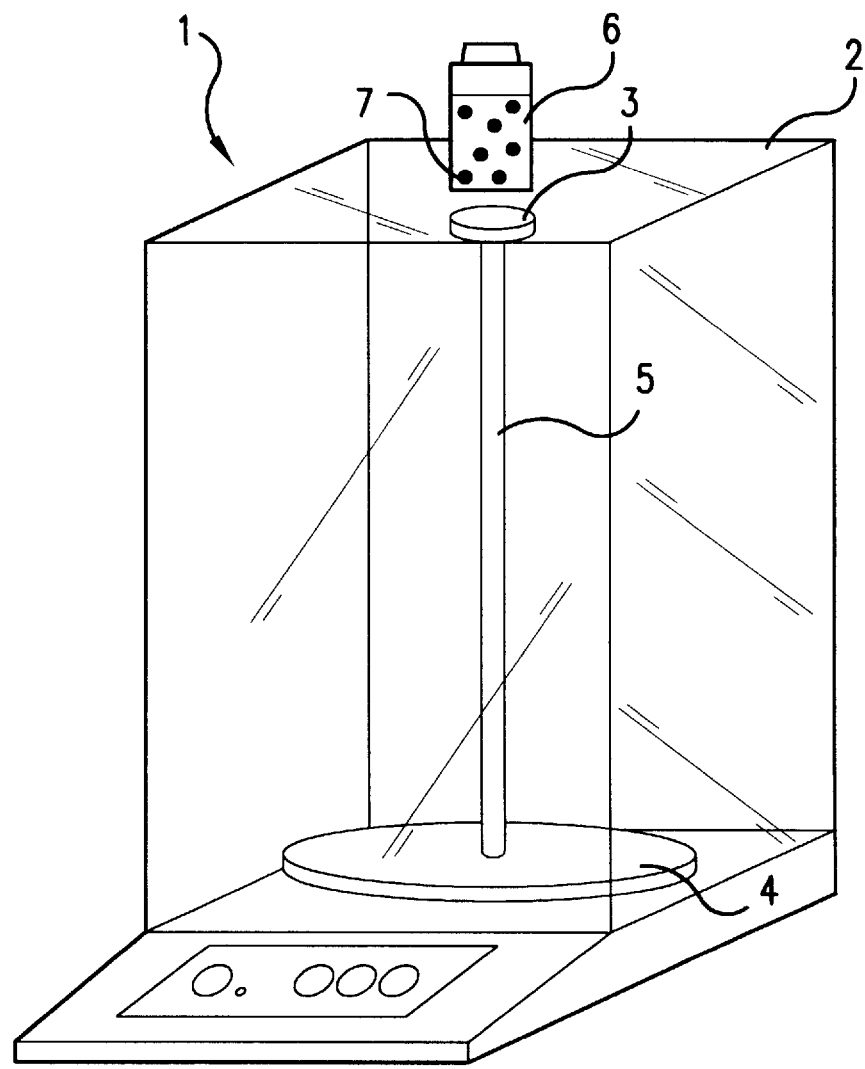
FIG. 1 represents a device for determining an analyte in a sample according to the invention, FIGS. 2a, –2c, 3a –3b and 4a –4c correspond to the curves representing the negative weighings expressed in arbitrary magnetic unit (in μg read on the balance), as a function of time, for anti-ferritin antibody concentrations of 100 μg, 25 μg and 10 μg per mg of metal particles, respectively. For each concentration, three dilutions, ⅕(a), ⅒ (b) and 1/20 (c) were tested, and for each dilution, three tests are performed: one blank (represented on the curves by ■), one test with 10 μl of ferritin (represented on the curves by □), and a test with 50 μl of ferritin (represented on the curves by ♦).
Figure 2A:
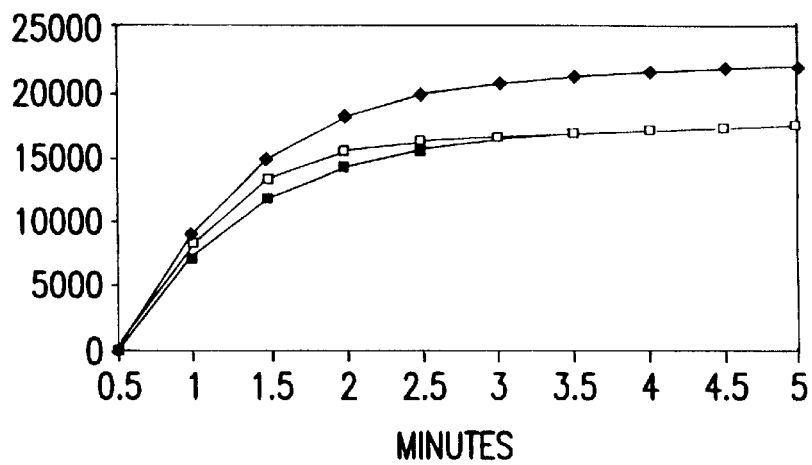
Figure 2B:
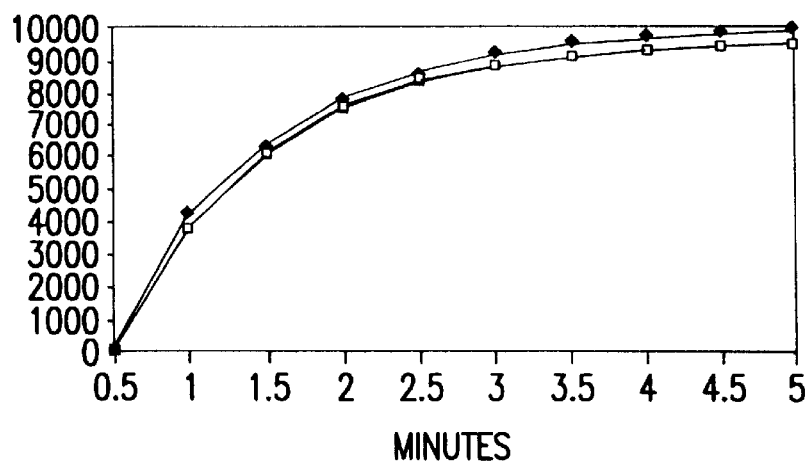
Figure 2C:
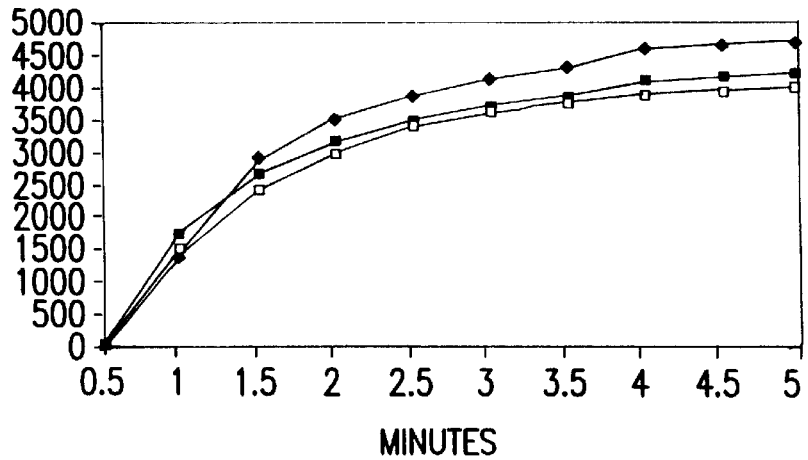
Figure 3A:
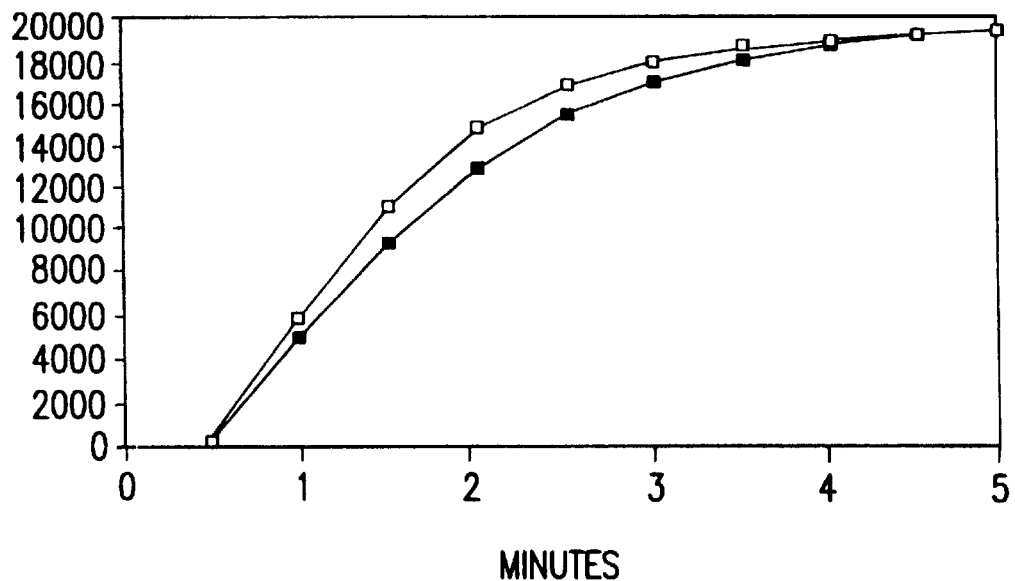
Figure 3B:
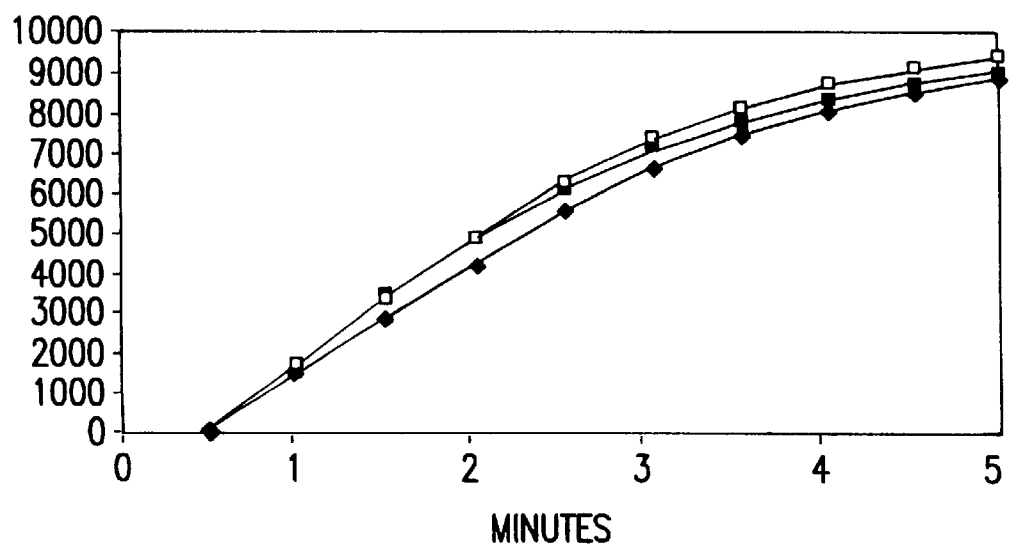
Figure 4A:
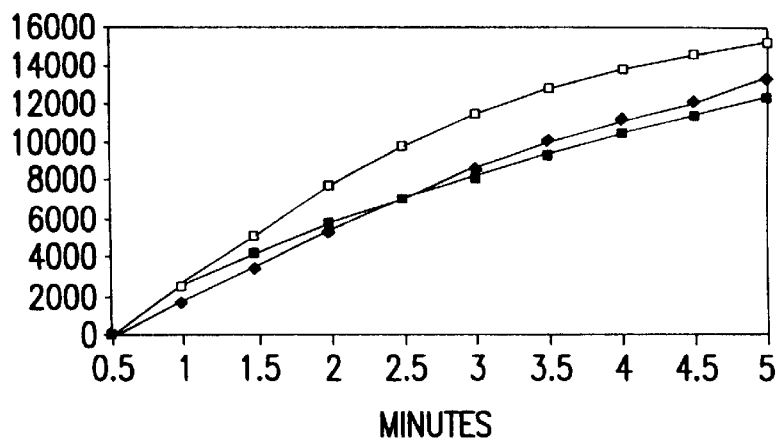
Figure 4B:
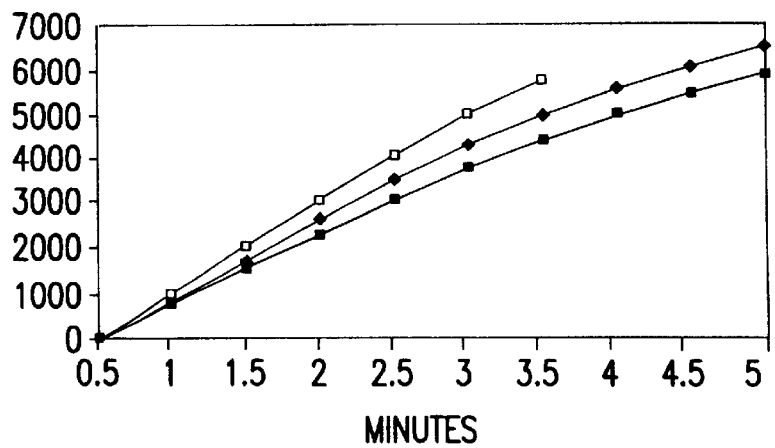
Figure 4C:
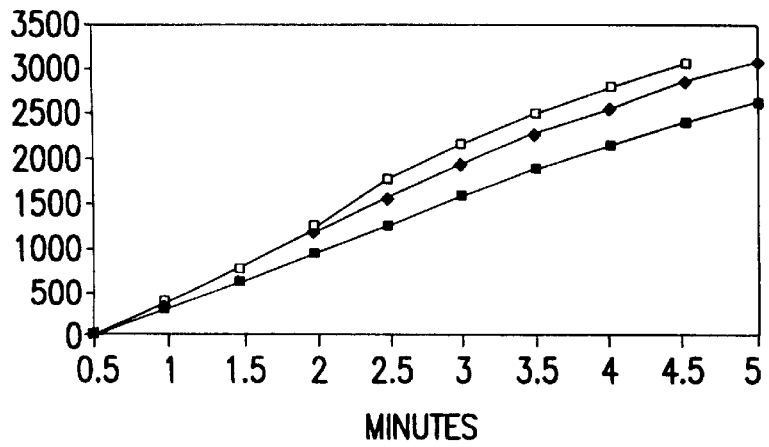

In accordance with FIG. 1, a device (1) of the invention consists of a standard commercial precision balance of the MeTTler MT5 type, under the top glass (2) of which is placed a magnet (3) 13 mm in diameter and 5 mm high, the magnet being integrally attached to the tray (4) of the balance through a nonmagnetic vertical axle (5). A container (6), which receives the sample to be determined, is placed on a sheet of aluminum placed over the magnet but without being in contact with it. The distance between the magnet and the vessel is 1 mm. The sample and the reagent (7) are brought into contact in the container (6).

EXAMPLE 1:

Determination of ferritin a) Synthesis of $Fe_3O_4$/Dextran T40 particles (50%)

14 grams of Dextran T40 (MW=40,000, Pharmacia) are added to 14 ml of water, and the Dextran is allowed to dissolve at room temperature in order to form a first solution.

A second solution is prepared with 3 grams of $FeCl_3 \cdot 6H_2O$ (MW=270.30) and 1.3 grams of $FeCl_2 \cdot 4H_2O$ (MW =198.81), in 20 ml of water.

The two solutions are introduced into a 250 ml double-jacketed reactor equipped with a stirring motor set to about 200-250 rpm, with a glass stirrer and a dropping funnel containing a 7.5% (v/v) $NH_4OH$ solution.

At room temperature, the 7.5% (v/v) $NH_4OH$ solution is added dropwise up to a final pH of between 10 and 11. The reactor is adjusted to 70° C. over about 60 minutes. At the end of the reaction, the solution is recovered and dialyzed thoroughly against 5 l of distilled water and then filtered on quartz wool. The solution is then centrifuged 3 times at 600 rpm for 5 minutes.

To remove the unreacted Dextran, the particles are deposited on 33×2.5 cm SEPHACRYL S300 HR gel column (Pharmacia), previously equilibrated with a 0.1M acetate buffer pH 6.5 , containing 0.15M NaCl and 0.05% $NaN_3$.

The metal particles obtained have an external diameter of between 20 and 900 nm, and preferably of between 50 and 70 nm, with a Dextran envelope. They are stored at +4° C.

b) Preparation of particles carrying an anti-ferritin antibody.

The particles are subjected to three dialyses against a PBS, (0.15M, 2 liters pH 6.8) buffer for 2, 4 hours and overnight respectively. These particles are oxidized, protected from light, for about 2 hours, by adding sodium periodate (0.1 M) for a final concentration in the reaction medium of 10 mM. The particles are then subjected to two additional dialyses against an NaCl solution (0.15M, 2 liters) for about 4 hours and overnight respectively. The pH is adjusted by adding $NaHCO_3$ to about 8. 100 µg of anti-ferritin antibodies (Bambou 8 produced by the company CLONATEC) are added to the solution containing the metal particles. The mixture is incubated for 5 hours overnight, at 25° C., with gentle stirring. The mixture thus formed is reduced by adding a sodium borohydride solution (for a final concentration of 20 mM in the total reaction medium), with gentle stirring for about 30 minutes. The mixture is dialyzed 3 times against 2 liters of a sodium phosphate (0.05M) -0.15M NaCl (0.15M) buffer, pH 7.5, for about 2 hours. The final solution contains 2.25 mg of metal particles per ml of solution, 10 to 100 µg of anti-ferritin per mg of particle.

c) Determination of ferritin

The solutions were tested as described below.

The solutions comprising 2.25 mg of particles per ml and 10, 25 and 100 µg of anti-ferritin/mg of particles, respectively, are tested after a ⅕, ⅒ and ½₀ dilution, respectively, by means of the device described in FIG. 1.

A 500 µl sample of each dilute solution is added to two glass tubes, respectively, to which 10 and 50 µl of ferritin (2000 mg/ml) are added respectively. The solutions are tested against a blank containing no ferritin. The magnetic force of attraction is measured over time. The values are negative weighing values given in arbitrary magnetic units.

The results are presented in the tables below.

Anti-ferritin antibody concentration: 100 µg/mg of particles

⅕ dilution

| Minutes | Blank | 10 µl | 50 µl |
| --- | --- | --- | --- |
| 0.5 | 0 | 0 | 0 |
| 1 | 7200 | 8270 | 8900 |
| 1.5 | 11760 | 13270 | 14800 |
| 2 | 14160 | 15320 | 18050 |
| 2.5 | 15550 | 16160 | 19850 |
| 3 | 16350 | 16620 | 20710 |
| 3.5 | 16850 | 16910 | 21280 |
| 4 | 17120 | 17080 | 21620 |
| 4.5 | 17330 | 17200 | 21850 |
| 5 | 17440 | 17300 | 22000 |

⅒ dilution

| Minutes | Blank | 10 µl | 50 µl |
| --- | --- | --- | --- |
| 0.5 | 0 | 0 | 0 |
| 1 | 3830 | 3770 | 4230 |
| 1.5 | 6070 | 6160 | 6420 |
| 2 | 7480 | 7570 | 7840 |
| 2.5 | 8320 | 8430 | 8660 |
| 3 | 8850 | 8880 | 9220 |
| 3.5 | 9160 | 9200 | 9550 |
| 4 | 9390 | 9390 | 9730 |
| 4.5 | 9550 | 9520 | 9890 |
| 5 | 9650 | 9600 | 9990 |

½₀ dilution

| Minutes | Blank | 10 µl | 50 µl |
| --- | --- | --- | --- |
| 0.5 | 0 | 0 | 0 |
| 1 | 1750 | 1510 | 1400 |
| 1.5 | 2670 | 2420 | 2880 |
| 2 | 3170 | 3000 | 3540 |
| 2.5 | 3500 | 3400 | 3880 |
| 3 | 3740 | 3630 | 4160 |
| 3.5 | 3900 | 3780 | 4340 |
| 4 | 4110 | 3910 | 4640 |
| 4.5 | 4190 | 3990 | 4720 |
| 5 | 4250 | 4070 | 4760 |

Anti-ferritin antibody concentration: 25 µg/mg of particles

⅕ dilution

| Minutes | Blank | 10 µl |
| --- | --- | --- |
| 0.5 | 0 | 0 |
| 1 | 4920 | 5800 |
| 1.5 | 9470 | 11200 |
| 2 | 13010 | 14830 |
| 2.5 | 15540 | 16950 |
| 3 | 17240 | 18160 |
| 3.5 | 18320 | 18830 |
| 4 | 19010 | 19250 |
| 4.5 | 19500 | 19530 |
| 5 | 19880 | 19730 |

⅒ dilution

| Minutes | Blank | 10 µl | 50 µl |
| --- | --- | --- | --- |
| 0.5 | 0 | 0 | 0 |
| 1 | 1540 | 1680 | 1360 |
| 1.5 | 3480 | 3340 | 2900 |
| 2 | 4900 | 4950 | 4200 |
| 2.5 | 6170 | 6380 | 5650 |
| 3 | 7160 | 7450 | 6800 |
| 3.5 | 7920 | 8240 | 7650 |
| 4 | 8480 | 8820 | 8280 |
| 4.5 | 8900 | 9200 | 8740 |
| 5 | 9210 | 9500 | 9110 |

½₀ dilution

| Minutes | Blank | 10 µl | 50 µl |
| --- | --- | --- | --- |
| 0.5 | 0 | 0 | 0 |
| 1 | 620 | 640 | 660 |
| 1.5 | 1230 | 1310 | 1300 |
| 2 | 1920 | 1960 | 1930 |
| 2.5 | 2479 | 2570 | 2510 |
| 3 | 2980 | 3080 | 3030 |
| 3.5 | 3410 | 3480 | 3450 |
| 4 | 3710 | 3780 | 3800 |
| 4.5 | 3960 | 4020 | 4050 |
| 5 | 4150 | 4190 | 4240 |

Anti-ferritin antibody concentration: 10 µg/mg of particles

1/5 dilution

| Minutes | Blank | 10 μl | 50 μl |
| --- | --- | --- | --- |
| 0.5 | 0 | 0 | 0 |
| 1 | 2550 | 2420 | 1740 |
| 1.5 | 4150 | 5020 | 3500 |
| 2 | 5600 | 7570 | 5220 |
| 2.5 | 6900 | 9620 | 6950 |
| 3 | 8100 | 11340 | 8560 |
| 3.5 | 9300 | 12670 | 9850 |
| 4 | 10350 | 13700 | 10930 |
| 4.5 | 1125 | 14420 | 11830 |
| 5 | 12150 | 15040 | 13170 |

1/10 dilution

| Minutes | Blank | 10 μl | 50 μl |
| --- | --- | --- | --- |
| 0.5 | 0 | 0 | 0 |
| 1 | 770 | 1000 | 840 |
| 1.5 | 1590 | 2070 | 1780 |
| 2 | 2300 | 3070 | 2650 |
| 2.5 | 3090 | 4080 | 3540 |
| 3 | 3810 | 5020 | 4330 |
| 3.5 | 4430 | 5780 | 5000 |
| 4 | 5000 | | 5640 |
| 4.5 | 5490 | | 6120 |
| 5 | 5920 | | 6550 |

1/20 dilution

| Minutes | Blank | 10 μl | 50 μl |
| --- | --- | --- | --- |
| 0.5 | 0 | 0 | 0 |
| 1 | 287 | 364 | 350 |
| 1.5 | 595 | 734 | 776 |
| 2 | 920 | 1211 | 1163 |
| 2.5 | 1238 | 1758 | 1563 |
| 3 | 1563 | 2143 | 1938 |
| 3.5 | 1876 | 2499 | 2301 |
| 4 | 2155 | 2814 | 2568 |
| 4.5 | 2400 | 3074 | 2889 |
| 5 | 2628 | | 3103 |

EXAMPLE 2

Determination of Listeria bacteria in a biological sample a) The metal particles used for this example were prepared in accordance with the procedure described in Example 1.

b) Preparation of particles carrying at least one antibody directed against Listeria, called hereinafter anti-L Ab.

The particles synthesized according to a) of Example 1 are oxidized, by adding sodium periodate (0.1M).

After stirring for 45 minutes, protected from particles are dialyzed against 0.15M NaCl for 4 hours.

10 μg/ml of anti-L Ab are added to the solution containing the metal particles, whose concentration is 1 mg of particles per mg of reagent; the pH is adjusted by adding $HCO_3$ to about 8.

The mixture is incubated for 20 hours, with gentle stirring. The mixture thus formed is reduced by adding a sodium borohydride solution, in a concentration of $12 \times 10^{-3}$ moles $NaBH_4$ per mg of particles, with gentle stirring for 45 minutes. The mixture is dialyzed over-night against a sodium phosphate (0.1M) —NaCl (0.15M) buffer at pH 7.5.

The final solution contains 0.415 mg of metal particles per ml of reagent, 15.4 μg of anti-L Ab per mg of particles, that is to say about 6.4 μg anti-L Ab per ml of reagent.

c) Determination of Listeria bacteria

The reagent is tested on a heart/brain broth, identified by the reference: L. INNO ATCC, 410A 4, Lot/Ch-b 390853.

The determination is as in Example 1, carried out on a METTLER MT5 balance under the following conditions: Po Container: glass tube 10 mm in diameter and 48 mm high, Po Magnet: 13 mm in diameter and 5 mm high, north directed upwards Po Distance magnet-tube: 1 mm (approximately)

A first solution called T2, comprising 500 μl of the reagent described in b) and 10 μl of broth was tested after stirring and incubating, then a second solution, called T3, comprising 500 μl of the reagent described in b), and which will be used as control, was tested.

The results presented in the following table correspond to the values for the measurement of the magnetic force of attraction read at times To and To +4 hours, time To being the time at the beginning of the reaction, that is to say of positioning the container above the magnet.

| Reaction time | T2 | T3 |
| --- | --- | --- |
| To | −6000 | −6000 |
| To + 4h | −18000 | −6000 |

The magnetic force of attraction of the metal clusters in sample T2 is therefore -12000, and will be correlated with the bacteria concentration by means of a calibration curve.

We claim:

1. A method for determining an analyte in a sample which comprises:
   i) providing said sample in liquid phase, the analyte of which comprises a ligand having at least one anti-ligand specific recognition site;
   ii) providing at least one reagent containing metal particles, in suspension in liquid phase and non-separable from said liquid phase by magnetic or electromagnetic means, and each metal particle containing a metal core to which at least one anti-ligand is fixed directly or indirectly;
   iii) contacting the sample and said at least one reagent containing metal particles, in order to obtain metal clusters;
   iv) placing the metal clusters into a magnetic field generated by a magnetic field generating sensor, in order to assemble the metal clusters; and
   v) subjecting said sensor to a force caused by the assembled metal clusters, giving a movement or force signal representative of the mass of said assembled metal clusters, correlated with the quantity of analyte present in the sample initially.

2. The method as claimed in claim 1, wherein the magnetic field generating sensor is integrally attached to a tray of a balance, and the metal mass is measured by negative weighing, that is to say by measuring the lightening of said tray.

3. The method as claimed in claim 1, wherein said at least one reagent comprises:
   a primary reagent comprising metal particles in suspension in liquid phase, non-separable from said liquid phase by magnetic means, and each metal particle comprising a metal core to which is fixed directly or indirectly at least one anti-ligand capable of reacting with a recognition site of the analyte ligand; and
   a secondary reagent comprising metal particles in suspension in liquid phase and non-separable from said liquid phase by magnetic means, and each metal particle containing a metal core to which is affixed directly or indirectly at least one other anti-ligand capable of reacting with another recognition site of the analyte ligand.

4. The method as claimed in claim 1, wherein the analyte ligand comprises at least two recognition sites of the reagent anti-ligand which are sufficiently far apart from each other to allow the same ligand to be combined with two-anti-ligands.

5. The method as claimed in claim 4, wherein the analyte ligand comprises at least two identical recognition sites of the reagent anti-ligand.

6. The method as claimed in claim 1, wherein the reagent anti-ligand comprises two receptor sites of the analyte ligand which are sufficiently far apart from each other to allow the same anti-ligand to be combined with two ligands.

7. The method as claimed in claim 1, wherein the reagent anti-ligand comprises at least two receptor sites, and the analyte ligand comprises at least two recognition sites which are specific for the two receptor sites of the reagent respectively.

8. The method as claimed in claims 3 and 5, wherein the primary reagent and the secondary reagent are identical.

9. The method as claimed in claim 1, according to which the analyte is determined by competition, wherein a competition reagent is provided containing metal particles in suspension in liquid phase and non-separable from said liquid phase by magnetic means, and each metal particle comprising a metal core to which is fixed directly or indirectly another ligand specifically recognized by the reagent anti-ligand.

10. A device for determining an analyte in a sample, comprising:

i) a container for receiving a sample to be determined in liquid phase, the analyte of which comprises a ligand having at least one anti-ligand specific recognition sites;

ii) at least one reagent comprising metal particles in suspension, in liquid phase and non-separable from said liquid phase by magnetic means, and each metal particle containing a metal core to which is fixed directly or indirectly at least one anti-ligand, having at least one receptor site of a ligand, the sample and said at least one reagent containing metal particles being contacted in said container, in order to obtain metal clusters; and iii) means for assembling and detecting the metal clusters, in order to obtain a signal representative of the mass of metal in the clusters, correlated with the quantity of analyte present in the sample initially, wherein said means comprises a magnetic field generating, sensor placed close to the sample, which generates a magnetic field in which the metal clusters are placed in order to assemble them and which is moved or subjected to a force caused by said assembled metal clusters, giving a movement or force signal representative of the mass of the metal in the clusters.

11. The device as claimed in claim 10, wherein the magnetic field generating sensor is integrally attached to a tray of a balance which delivers a negative weighing signal corresponding to the lightening of said tray, and representative of the metal mass of the clusters.

12. The method according to claim 1, wherein the sample and the reagent are contacted by incubation.

13. The device according to claim 10, wherein the sample and the reagent are contacted by incubation.

14. The method according to claim 1, wherein the metal core of said metal particles have a mean size in a range from 5 nm to 30 nm.

15. The method according to claim 1, wherein the metal core of said metal particles have a mean size in a range from 10 nm to 20 nm.

16. The device according to claim 10, wherein the metal core of said metal particles have a mean size in a range from 5 nm to 30 nm.

17. The device according to claim 10, wherein the metal core of said metal particles have a mean size in a range from 10 nm to 20 nm.

* * * * *